US012415772B1

(12) United States Patent
Alexander et al.

(10) Patent No.: US 12,415,772 B1
(45) Date of Patent: Sep. 16, 2025

(54) SYSTEM AND METHOD FOR PRODUCTION OF SYNTHETIC FATTY ACIDS (71) Applicant: Savor Foods Limited, San Jose, CA (US)

(72) Inventors: Kathleen Alexander, San Jose, CA (US); Ian McKay, San Jose, CA (US)

(73) Assignee: Savor Foods Limited, San Jose, CA (US)

( * ) Notice: Subject to any disclaimer, the term of this patent is extended or adjusted under 35 U.S.C. 154(b) by 583 days.

(21) Appl. No.: 17/825,490

(22) Filed: May 26, 2022

Related U.S. Application Data (60) Provisional application No. 63/193,292, filed on May 26, 2021.

(51) Int. Cl.
| | | |
|---|---|---|
| C07C 2/12 | (2006.01) |
| B01J 23/75 | (2006.01) |
| C01B 32/40 | (2017.01) |
| C07C 1/04 | (2006.01) |
| C07C 4/06 | (2006.01) |
| C07C 51/16 | (2006.01) |

(Continued)

(52) U.S. Cl.
CPC ............ C07C 67/08 (2013.01); B01J 23/75 (2013.01); C01B 32/40 (2017.08); C07C 1/0435 (2013.01); C07C 1/0485 (2013.01); C07C 4/06 (2013.01); C07C 51/16 (2013.01); C11C 1/10 (2013.01); C11C 3/006 (2013.01); C11C 3/02 (2013.01); C25B 1/23 (2021.01); C25B 15/081 (2021.01); C07C 2523/75 (2013.01)

(58) Field of Classification Search
CPC ..... C07C 67/08; C07C 1/0435; C07C 1/0485; C07C 4/06; C07C 51/16; C07C 2523/75; C01B 32/40; C25B 15/081; C25B 1/23; B01J 23/75; C11C 1/10; C11C 3/006; C11C 3/02
USPC .......................................................... 426/607
See application file for complete search history.

(56) References Cited

U.S. PATENT DOCUMENTS

| | | |
|---|---|---|
| 2,054,096 A | 9/1936 | Potts et al. |
| 2,835,691 A | 5/1958 | Sauter |

(Continued)

FOREIGN PATENT DOCUMENTS

| | | | |
|---|---|---|---|
| WO | WO-2013126990 A1 * | 9/2013 | ............. A61K 31/22 |
| WO | 2023076737 A1 | 5/2023 | |

OTHER PUBLICATIONS

Barton, Derek H. R., et al., "The Conversion of Saturated Hydrocarbons into Carboxylic Acids using Fe(CO) 5-H20 2 Oxidation", Tetrahedron Letters, vol. 37, No. 45, pp. 8137-8140, 1996.

(Continued)

*Primary Examiner* — Brent T O'Hern
(74) *Attorney, Agent, or Firm* — Jeffrey Schox; Randy Mehlenbacher (57) ABSTRACT

A method for producing a fatty acid can include: receiving a hydrocarbon sample derived from at least one of carbon dioxide, methane, coal, biomass, or other suitable carbon feedstock, oxidizing the hydrocarbon sample to form oxygenated hydrocarbons, optionally separating different oxygenated species from the oxygenated hydrocarbons, optionally fractioning the oxygenated hydrocarbons, and optionally esterifying the oxygenated hydrocarbons such as to form triglycerides.

20 Claims, 4 Drawing Sheets

(51) Int. Cl.
    *C07C 67/08*     (2006.01)
    *C11C 1/10*     (2006.01)
    *C11C 3/00*     (2006.01)
    *C11C 3/02*     (2006.01)
    *C25B 1/23*     (2021.01)
    *C25B 15/08*     (2006.01)

(56) References Cited

U.S. PATENT DOCUMENTS

| | | | |
|---|---|---|---|
| 3,413,323 | A | 11/1968 | Berry |
| 5,670,540 | A | 9/1997 | Horrobin et al. |
| 10,327,452 | B2 | 6/2019 | Lao et al. |
| 2007/0277430 | A1 | 12/2007 | Jackman et al. |
| 2021/0324301 | A1 | 10/2021 | Lorén et al. |
| 2025/0059463 | A1 | 2/2025 | Alexander et al. |

OTHER PUBLICATIONS

Davis, Steven J., et al., "Food without agriculture", Nature Sustainability, https://doi.org/10.1038/s41893-023-01241-2, Published: Nov. 6, 2023.

García Martínez, Juan B., et al., "Food without agriculture: Food from CO2, biomass and hydrocarbons to secure humanity's food supply against global catastrophe", Trends in Food Science & Technology 150 (2024) 104609.

García Martínez, Juan B., et al., "Synthetic fat from petroleum as a resilient food for global catastrophes: Preliminary techno-economic assessment and technology roadmap", Chemical Engineering Research and Design 177 (2022) 255-272.

Gibon, V., "Fractionation of lipids for use in food", In the book Modifying lipids for use in food, pp. 201-233, Sep. 2006.

Gilmer, Chad M., "Separation of Saturated Fatty Acids and Fatty Acid Methyl Esters with Epoxy Nanofiltration Membranes", RSC Adv. 2017 ; 7: 55626-55632. doi: 10.1039/C7RA11223H.

Raine, T. L., et al., "The Oxidation of Hydrocarbons, Part I. the Carboxylic Acids Formed in the Slow Oxidation of n-Heptane", Transactions of the Faraday Society, vol. 47, 1951.

"Additional Informational Concerning the Fischer-Tropsch Process and Its Products, Synthetic Fatty Acids and Detergents", BIOS Final Report No. 1722. Objectives Sub-Committee. B.I.O.S.British Intelligence Objectives Subcommittee (BIOS) Published by British Intelligence Objectives Subcommittee (BIOS). HMSO., London. England, 1947.

"Additional Informational Concerning the Fischer-Tropsch Process and Its Products, Table of Contents", BIOS Final Report No. 1722, British Intelligence Objectives Subcommittee (BIOS) Published by British Intelligence Objectives Subcommittee (BIOS). HMSO., London. England., 1947.

"Study and Methods for Chemical Synthesis of Edible Fatty Acids and Lipids", Final Technical Report, National Aeronautics and Space Administration, Washington, D.C., Jul. 1968.

Anneken, David J., et al., "Fatty Acids", Wiley-VCH Verlag Gmbh & Co. KGaA, Weinheim, 2012, vol. 14, pp. 77-116.

Chaux, R., "Synthetic Soap and Edible Fats", Abstracts of Literature, vol. 54, 1946, p. 308.

De Klerk, Arno, "Thermal Cracking of Fischer-Tropsch Waxes", Ind. Eng. Chem. Res. 2007, 46, 5516-5521.

Emanuel, N.M., "The Oxidation of Hydrocarbons in the Liquid Phase", Book, 1965.

Fineberg, H., et al., "Synthetic Fatty Acids", J. Am. Oil Chemists' SOC, Nov. 1979 (vol. 56).

Krishfield, Laura, "Case Study: Swedish Researchers Identify Fat as the Newest Opportunity for CO2 Derived Ingredients", Lux Research, Nov. 2021.

Layman, Patricia L., "Oleochemicals Fashion Long-Term Optimism from Near-Term Gloom", Oct. 10. 1983 C&EN.

Nooner, D.W., et al., "Synthesis of Fatty Acids by a Closed System Fischer-Tropsch Process", 1979 American Chemical Society.

Petersen, Anna P., et al., "Cobalt-Based Fischer-Tropsch Synthesis: A kinetic Evaluation of Metal-Support Interactions Using an Inverse Model System", Catalysts 2019, 9, 794.

Rushdi, Ahmed I., et al., "Lipid formation by aqueous Fischer-Tropsch-type synthesis over a temperature range of 100 to 4000° C", Origins of Life and Evolution of Biospheres, Jan. 2001.

Scheidler, Christopher, et al., "Unsaturated C3,5,7,9-Monocarboxylic Acids by Aqueous, One-Pot Carbon Fixation: Possible Relevance for the Origin of Life", Scientific Reports, Mar. 9, 2016.

Tomasek, Szabina, et al., "Hydrocracking of Fischer-Tropsch Paraffin Mixtures over Strong Acid Bifunctional Catalysts to Engine Fuels", ACS Omega 2020, 5, 25413-26420.

Campos, R.J., et al., "Fractionation of Milk Fat by Short-Path Distillation", J. Dairy Sci. 86:735-745, received Jun. 7, 2002.

Deffense, E., "Milk Fat Fractionation Today: A Review", American Oil Chemists' Society, vol. 70, No. 12 (Dec. 1993).

Romano, Raffaele, et al., "Triacylglycerols, fatty acids and conjugated linoleic acids in Italian Mozzarella di Bufala Campana cheese", Journal of Food Composition and Analysis 24 (2011) 244-249, Dec. 8, 2010.

\* cited by examiner

Chain length (number of carbon atoms)
FIGURE 4C

SYSTEM AND METHOD FOR PRODUCTION OF SYNTHETIC FATTY ACIDS

CROSS-REFERENCE TO RELATED APPLICATIONS

This application claims the benefit of U.S. Provisional Application No. 63/193,292, filed 26 May 2021, which is incorporated in its entirety by this reference.

TECHNICAL FIELD

This invention relates generally to the fatty acid synthesis field, and more specifically to a new and useful system and method in the fatty acid synthesis field.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview

Figure 1:
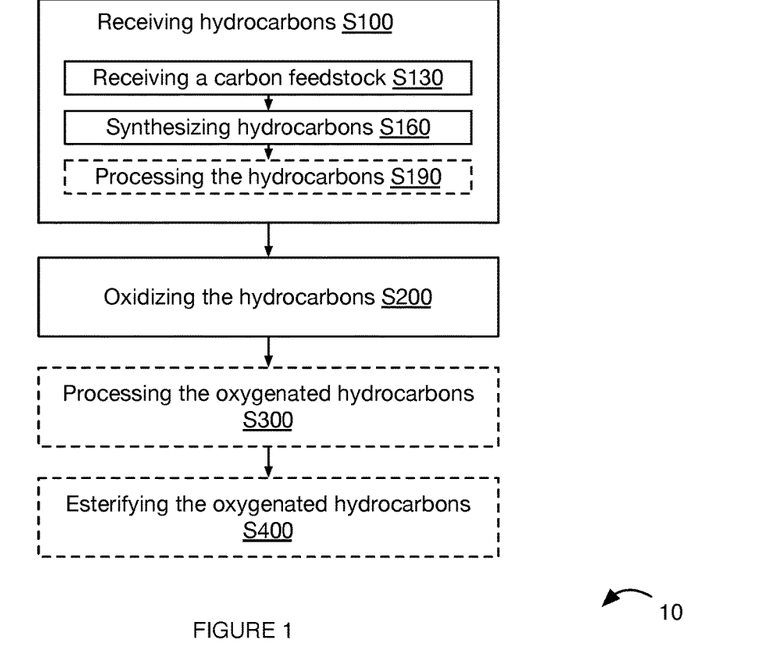
FIG. 1 is a schematic representation of the method.

As shown in FIG. 1, the method can include receiving a hydrocarbon sample S100 and oxidizing the hydrocarbon sample S200. The method can optionally include processing the oxidized hydrocarbons S300, esterifying the oxygenated hydrocarbons S400, and/or any suitable steps. Receiving a hydrocarbon sample can include receiving a carbon feedstock S130, synthesizing hydrocarbons from the carbon feedstock S160, processing the hydrocarbons S190, and/or any suitable steps and/or processes.

The method preferably functions to form (e.g., synthesize, generate, produce, manufacture, etc.) fatty acids and/or fatty acid derivatives (e.g., monoglycerides, diglycerides, triglycerides, glycerophospholipids, fatty amines, fatty acid amides, etc.). The fatty acids can be used, for example, in food (e.g., as a food source, as a functional food, in a formulation designed to mimic a fat, to provide a target nutritional composition, etc.), feedstock, as a fuel source (e.g., biodiesel), as a surfactant, as a biofuel, as an emollient, in cosmetics, as a lubricant, in soap, in a metallic soap, as an emulsifier, in detergents, in solvents, in bioplastics, and/or can be used for any purpose. The resulting fatty acids are preferably (but not necessarily) saturated. The resulting fatty acids are preferably (but not necessarily) unbranched (e.g., straight chain).

2. Benefits

Variations of the technology can confer several benefits and/or advantages.

First, variants of the technology can be beneficial for producing fatty acids (and/or derivatives thereof) with a low carbon intensity (e.g., without the use of agriculture). For example, by using inorganic carbon feedstocks (e.g., carbon dioxide, carbon monoxide, methane, ethane, ethene, ethyne, coal, etc.), fatty acids can be manufactured without requiring animals, plants, or other living organisms. This can lead to lower land-use, less water use, enhanced energy efficiency, and/or can otherwise facilitate a low carbon intensity (e.g., small carbon footprint). In some variations, the carbon intensity can be negative (e.g., remove carbon dioxide, methane, etc. from the environment; trap carbon dioxide; etc.), can be less than a carbon intensity to derive a comparable mass of fatty acid from an agricultural source, and/or can have any suitable value. Relatedly, some of the resulting fatty acids may not be available or abundant from plants (e.g., stearic acid, arachidic acid, behenic acid, etc.), but can be produced in variants of the technology.

Second, variants of the technology can promote the formation of unbranched, saturated fatty acids. For example, depending on the catalyst, temperature, pressure, reactant ratio, reaction time, and/or any suitable process parameters, the composition (e.g., carbon chain length, carbon chain length distribution, isomer composition, etc.) of paraffins can be controlled (which can then impact the fatty acids derived therefrom). For instance, the use of a high-alpha cobalt catalyst can promote the formation of predominantly unbranched paraffins (e.g., >90%, >95% unbranched, >97%, >98%, >99%, >99.5%, >99.9%, >99.99%, >99.95%, >99.999%, etc. unbranched paraffins; <1000 ppm, <500 ppm, <100 ppm, <10 ppm, <1 ppm, <100 ppb, <10 ppb, <1 ppb, <100 ppt, <10 ppt, <1 ppt, etc. of branched paraffins; etc.).

Third, variants of the technology can enable economical production of fatty acids (e.g., while maintaining or achieving a low carbon intensity, without the use of agriculture, etc.).

However, variants of the technology can confer any other suitable benefits and/or advantages.

As used herein, "substantially" or other words of approximation (e.g., "about," "approximately," "predominantly," "primarily," etc.) can be within a predetermined error threshold or tolerance of a metric, component, or other reference (e.g., within 0.001%, 0.01%, 0.1%, 1%, 5%, 10%, 20%, 30%, etc. of a reference), or be otherwise interpreted.

4. Method

As shown in FIG. 1, the method 10 can include receiving a hydrocarbon sample S100 and oxidizing the hydrocarbon S200. The method can optionally include processing the oxidized hydrocarbon S300, esterifying the oxygenated hydrocarbon S400, and/or any suitable steps.

The method can be performed in a single-pot synthesis or a multi-pot synthesis. The method can be performed at a laboratory scale (e.g., ranging from producing and/or consuming masses of products or reactants between about 1 ng and 1 g), process scale (e.g., 1 g to 1 kg), bench scale (e.g., 1 kg to 100 kg), demonstration scale (e.g., greater than 100 kg), and/or on any suitable scale. The method (and/or steps thereof) can be performed in a batch reactor, continuous stirred-tank reactor, plug flow reactor, semi-batch reactor, catalytic reactor, and/or in any suitable tank, manifold (e.g., pipe, tube, etc.), and/or chemical reactor. For example, the method or steps thereof can be performed in a slurry reactor, fluidized bed reactor, and/or a fixed bed reactor. The method and/or steps thereof can be performed in a batch process, a continuous process, and/or in any suitable process.

Energy input into the method or steps thereof (e.g., electricity, heat, etc.) is preferably generated using a renewable energy source (e.g., one that does not substantially generate carbon, solar, wind, geothermal, hydropower, biofuels, etc.), which can be beneficial for achieving low carbon impact method (e.g., carbon neutral, carbon negative, etc.). However, energy can be provided via nonrenewable sources (e.g., fossil fuels, nuclear, etc.) and/or any suitable source.

The carbon utilization of the method (e.g., percentage of carbon atoms from carbon feedstock, hydrocarbon, etc. that are present in the resulting oxygenates, fatty acids, etc.) is preferably at least 40% (e.g., 40%, 45%, 50%, 60%, 70%, 75%, 80%, 85%, 90%, etc.). Having a carbon utilization of at least 40% can be beneficial for achieving a low carbon impact process. However, the carbon utilization can be less than 40%.

Receiving a hydrocarbon sample S100 functions to receive a starting material or feedstock for formation of fatty acids. The hydrocarbons can be received, for example, in an oxidation reactor (e.g., to be used to oxidize the hydrocarbons in S200), and/or can be received in any suitable container.

The hydrocarbon sample preferably includes saturated hydrocarbons, but can include unsaturated hydrocarbons. The hydrocarbon sample preferably includes paraffins (e.g., alkanes), but can additionally or alternatively include alkenes, alkynes, arenes, and/or any suitable hydrocarbons. In a specific example, the hydrocarbon sample consists essentially of alkanes (e.g., >90% alkanes, >95% alkanes, >98% alkanes, >99% alkanes, >99.9% alkanes, >99.99% alkanes, etc.). The hydrocarbons are preferably linear (e.g., straight-chain, unbranched, etc.), but can additionally or alternatively be nonlinear (e.g., branched, cyclic, etc.). In a specific example, the hydrocarbon sample can consist essentially of linear hydrocarbons (e.g., >90% linear, >95% linear, >98% linear, >99% linear, >99.9% linear, >99.99% linear, etc.; linear paraffins; n-paraffins; etc.). As a specific example, the hydrocarbon sample can consist of linear paraffins. However, any suitable hydrocarbon sample can be used (e.g., a sample that includes unsaturated hydrocarbons).

The hydrocarbon sample can be gas phase, liquid phase, solid phase, and/or can include any suitable phase or mixture thereof (e.g., at standard temperature and pressure, at room temperature such as 15-30° C., etc.).

Figure 4A:
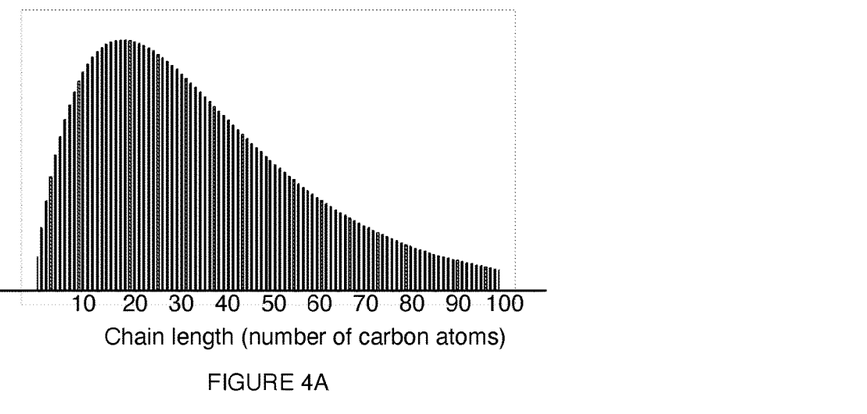
FIGS. 4A, 4B, and 4C are schematic representations of exemplary paraffin and/or oxygenated paraffin chain length (e.g., number of carbon atoms) distributions.
Figure 4B:
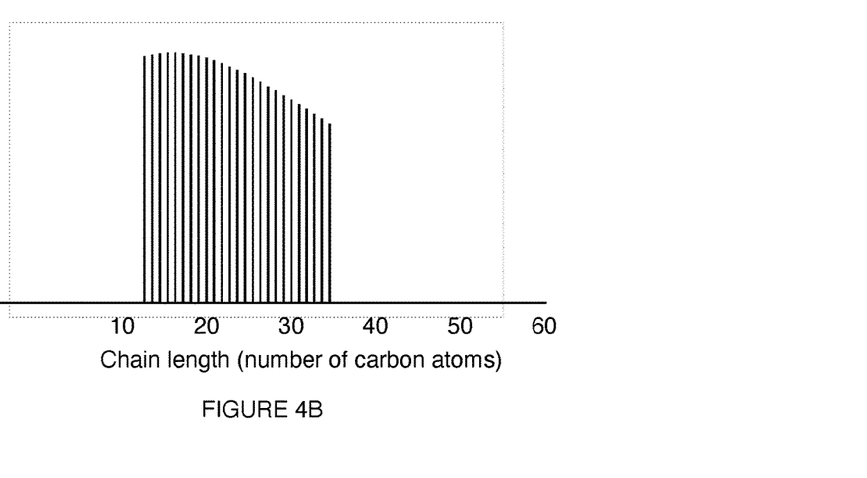
Figure 4C:
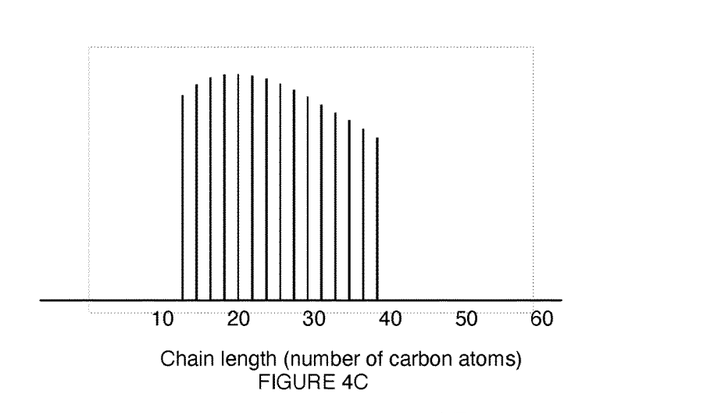

The hydrocarbon sample can include hydrocarbons with a distribution of chain lengths (e.g., number of carbon atoms). The distribution can be a normal distribution, an Anderson-Schulz-Flory distribution (e.g., as shown for example in FIG. 4A), Student's t distribution, uniform distribution, Poisson distribution, and/or can otherwise be distributed. The chain length can follow the distribution, can be bounded by a maximum and/or minimum chain length (e.g., follow the distribution for chain lengths less than a maximum length, follow the distribution for chain lengths longer than the minimum, follow the distribution between the maximum and minimum chain length, as shown for example in FIG. 4B or FIG. 4C, etc.), and/or can otherwise be bounded or unbounded. The hydrocarbon sample can include odd and even chain lengths, only odd chain lengths, only even chain lengths (e.g., as shown for example in FIG. 4C), specific chain lengths (e.g., C6-C100, C18-C28, C16-C40, C5-C10 and C14-C30, C10-C20, C1-C40, C1-C200, any range or combinations of ranges contained therein, etc.), and/or any suitable chain lengths (e.g., number of carbon atoms). A peak of the distribution is preferably between about C18 and C28, but the distribution can peak at any suitable carbon length. As an illustrative example, the hydrocarbon sample can include hydrocarbons with between 6 and 100 carbon atoms. In another illustrative example, the hydrocarbon sample can include hydrocarbons with between 12 and 40 carbon atoms (e.g., inclusive of all or any subset of chain lengths between 12 and 40, as shown for example in FIG. 4B, only even chain lengths between 12 and 40, as shown for example in FIG. 4C, etc.). In another illustrative example, the hydrocarbon sample can include hydrocarbons with chain lengths between about 18 and 28. However, any suitable chain length hydrocarbons can be used.

The hydrocarbon sample can be recycled (e.g., recovered as a byproduct from another process), pristine (e.g., synthesized expressly for use in the method), and/or can otherwise be prepared.

In some variants, receiving hydrocarbons can include receiving a carbon feedstock S130, synthesizing hydrocarbons from the carbon feedstock S160, processing the hydrocarbons S190, and/or any suitable steps and/or processes.

Receiving a carbon feedstock S130 functions to receive a feedstock to be used to synthesize the hydrocarbons. The carbon feedstock is preferably synthesis gas (e.g., a mixture of carbon monoxide and hydrogen, 'syngas,' etc.), but can additionally or alternatively include carbon dioxide, carbon (e.g., inorganic carbon such as nanocarbon, graphite, coal, etc.; organic carbon such as polymers, plastics, biomass, etc.; etc.), methane, natural gas, biogas, mixed municipal solid waste, recycled plastic streams, recycled paper streams, and/or any suitable carbon feedstock can be used. The syngas preferably has an $H_2$ to CO ratio (e.g., mass ratio, volume ratio, etc.) that is between about 1.5 and 2.5, but can have a ratio less than 1.5 or greater than 2.5. The carbon feedstock can be provided in a reactor (e.g., oxidation reactor, polymerization reactor, Fischer-Tropsch reactor, hydrogenation reactor, electrolysis reactor, steam methane reformation reactor, etc.), and/or in any suitable container.

In variants, receiving a carbon feedstock can include transforming the carbon feedstock into synthesis gas. However, the carbon feedstock can additionally or alternatively be transformed into olefins (e.g., ethene, propene, alkenes, etc.), acetylenes (e.g., ethyne, propyne, alkynes, etc.), and/or any suitable carbon precursor for synthesizing a hydrocarbon sample.

For example, a carbon feedstock can undergo gasification (e.g., dehydration at about 100° C., pyrolysis at around 200-300° C., combustion, gasification, water-gas shift reaction, etc.) to form carbon monoxide, carbon dioxide, water, hydrogen, and/or any suitable products. The gasification reaction can be performed in a counter-current fixed bed gasifier, a co-current fixed bed gasifier, a fluidized bed reactor, an entrained gasifier, a plasma gasifier, and/or any suitable reactor can be used.

Figure 2A:
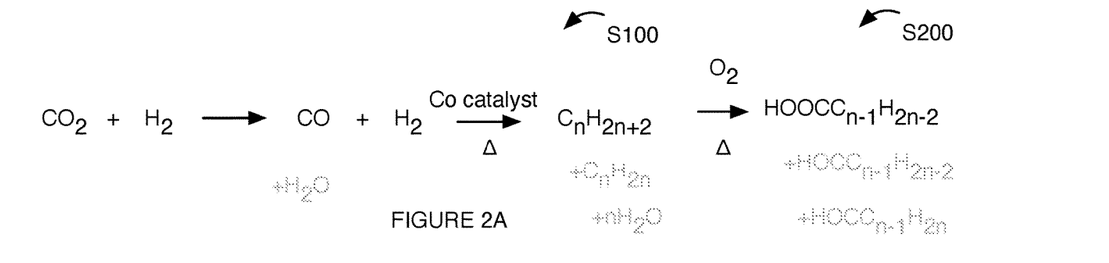
FIGS. 2A and 2B are schematic representations of examples of synthesizing paraffins.
Figure 2B:
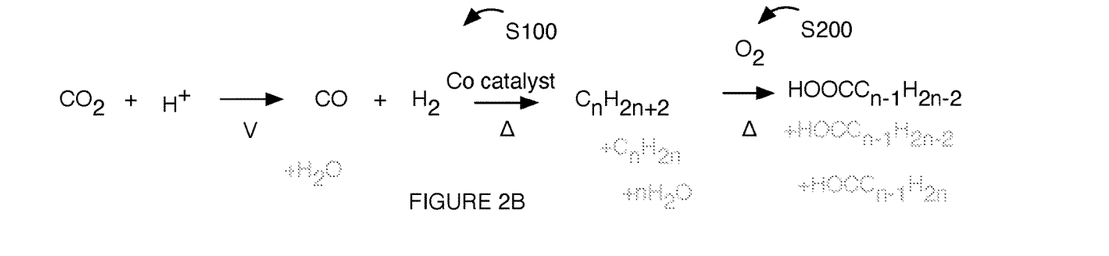

In another example, transforming carbon feedstock into synthesis gas can include reducing carbon dioxide (e.g., captured carbon dioxide, carbon dioxide produced during a gasification reaction, etc.) into carbon monoxide. Carbon dioxide can be reduced using hydrogenation (e.g., reverse water gas shift, as shown for example in FIG. 2B), electrolysis (as shown for example in FIG. 2A), and/or using any suitable reduction. For instance, carbon dioxide can be electrolytically reduced to carbon monoxide using a solid oxide electrolyzer cell, using a catalyst (e.g., porphyrin catalyst, cobalt catalyst, phytocyanine catalyst, silver catalyst, gold catalyst, zinc catalyst, nickel cyclam, metal phosphine, etc.), and/or in any manner. The electrolytic reduction (e.g., $CO_2 + 2\ H^+ + 2\ e^- \leftrightarrows CO + H_2O$) is typically performed at an electrical potential between about −0.5V and −1V, but can be performed at any suitable electrical potential. The reverse water gas shift reaction (e.g., $CO_2 + H_2 = CO + H_2O$) can be performed using a copper-based catalyst, noble metal catalyst (e.g., supported on metal oxide), reducible oxide support catalyst, transition metal carbide catalyst, and/or any suitable catalyst. The reverse water-gas-shift reaction is preferably performed at a temperature between about 500 and 800° C., but can be performed at any suitable temperature. The reverse gas shift reaction is preferably performed at a pressure between about 0-5 bar, but can be performed at any suitable pressure. However, any suitable carbon dioxide reduction can be performed.

In another example, methane can be oxidized to form carbon monoxide (and/or carbon dioxide which can then be reduced such as in a manner as described above). For instance, methane can be oxidized using steam methane reforming (e.g., $CH_4 + H_2O \leftrightarrows CO + 3\ H_2$). The steam methane reforming reaction is preferably performed at a temperature between about 800 and 1000° C., but can be performed at a temperature below 800° C. and/or above 1000° C. The steam methane reforming reaction is preferably performed at a pressure between about 20-30 bar, but can be performed at pressures less than 20 bar or greater than 30 bar. The ratio of water to methane (e.g., S/C ratio) in the steam methane reforming reaction is preferably between 2.5:1 and 3:1 (e.g., with excess water), but can be less than 2.5:1 or greater than 3:1. The steam methane reforming can be performed using nickel catalyst, nickel-alumina catalyst, rhodium catalyst, platinum catalyst, and/or using any suitable catalyst (e.g., where the catalyst shape can be spoked wheel, gear wheel, rings with holes, Raschig rings, etc. with high surface area). However, any suitable conditions can be used (e.g., to promote a different equilibrium composition).

In another example, one or more of the preceding examples can be combined. For instance, carbon monoxide can be produced from a combination of one or more of methane, carbon dioxide, and/or carbon (e.g., coal). However, any suitable carbon feedstock(s) can be used.

The carbon feedstock (e.g., carbon precursor, carbon source, etc.) can be pristine carbon (e.g., mined, drilled, fracked, recovered from Earth, etc.), recycled carbon (e.g., generated from another industrial process, captured carbon, recycled from other steps of the method, etc.), and/or any suitable carbon feedstock can be used. For example, carbon can be captured (e.g., from the atmosphere, from the ocean, from industrial processes, from a sequestration source, etc.) using membrane technology, oxyfuel combustion, absorption (e.g., carbon scrubbing, amine, zeolite, metal organic framework, etc.), multiphase absorption, adsorption, chemical looping combustion, calcium looping, cryogenic, and/or using any suitable technology. However, any suitable carbon capture can be used. In an illustrative example of recycling products from the method, short and/or long chain paraffins (and/or oxygenates derived therefrom) can be used as a carbon feedstock (e.g., can be gasified to produce syngas). In another example of recycling a feedstock, hydrogen from steam methane reforming can be used to reduce carbon dioxide and/or can be mixed with the syngas for paraffin synthesis. In another example of recycling a feedstock, water can be split (e.g., using electrolysis, photocatalytic water splitting, thermal decomposition, etc. where energy is preferably but not necessarily provided from a renewable source) to produce hydrogen (e.g., for reducing $CO_2$, for syn gas formation, etc.) and the resulting oxygen can be used in the hydrocarbon oxidation. However, the feedstock can otherwise be recycled.

In some variants, receiving a carbon feedstock can include receiving hydrogen (e.g., to be mixed with carbon monoxide to form synthesis gas). The hydrogen is preferably from a renewable and/or low impact carbon source. Examples of preferred hydrogen include: green hydrogen (e.g., derived from water electrolysis, preferably employing renewable electricity), turquoise hydrogen (e.g., derived from thermal splitting of methane), purple hydrogen (e.g., made using nuclear power and heat to drive chemothermal electrolysis of water), pink hydrogen (e.g., derived from water electrolysis, employing electricity derived from nuclear power plant), red hydrogen (e.g., derived from the high temperature catalytic splitting of water using nuclear power thermal energy), yellow hydrogen (e.g., derived from water electrolysis driven by solar energy), or white hydrogen (e.g., naturally occurring hydrogen, hydrogen as a byproduct of industrial processes, etc.). However, additionally or alternatively, blue hydrogen (e.g., sourced from fossil fuels with capture or sequestration of carbon), gray hydrogen (e.g., produced from fossil fuels such as using steam methane reforming), black hydrogen (e.g., produced from gasification of bituminous coal), brown hydrogen (e.g., produced from gasification of lignite coal), and/or any suitable hydrogen source can be used (e.g., where carbon generated in these processes can be used as a carbon feedstock). However, any suitable hydrogen source can be used. In some variants, the hydrogen can be formed on site (e.g., in the same location as the carbon feedstock is processed, at the same location as the paraffin synthesis, at the same location as oxidation, etc.). However, the hydrogen can be formed at any suitable location (e.g., to be transported to a processing site).

In some variants, the feedstocks (e.g., carbon feedstock, hydrogen feedstock, etc.) can be cleaned (e.g., purified) which can function to remove one or more species from the feedstock(s). For example, feedstocks can be desulphurized (e.g., to have Sulphur removed so that it does not poison a catalyst) such as by using a scavenger (e.g., amine treatment, Claus process, tail gas treatment, etc.). However, the feedstocks can be cleaned in any manner. The feedstocks are preferably cleaned before forming syngas, but can be cleaned during and/or after forming syngas.

Synthesizing hydrocarbons S160 functions to produce a hydrocarbon sample that is to be oxidized. The hydrocarbon sample is preferably synthesized to be as described above, but can be processed (e.g., undergo cracking, separation, fractionation, etc. to meet the described hydrocarbon sample) and/or can have any suitable distribution as synthesized. The hydrocarbon sample is preferably synthesized using a Fischer-Tropsch (e.g., a modified Fischer-Tropsch) process, but can additionally or alternatively be synthesized using a Ziegler process (e.g., a modified Ziegler process), the Guerbet reaction, and/or using any suitable processes and/or reactions.

In variants of synthesizing the hydrocarbons using a Fischer-Tropsch (FT) process, a high-alpha catalyst is preferably used. A high-alpha catalyst can refer to a catalyst that promotes the formation of a distribution of hydrocarbons with an Anderson-Schulz-Flory distribution where the parameter alpha is greater than about 0.5 (e.g., a value or range thereof such as 0.5, 0.55, 0.6, 0.65, 0.7, 0.75, 0.8, 0.85, 0.9, 0.95, 0.97, 0.98, 0.99, 0.995, 0.999, 0.9995, 0.9999, 1, etc.). However, a high-alpha catalyst can otherwise be defined (e.g., as a catalyst that promotes formation or generation of hydrocarbons with greater than a single carbon atom, as a catalyst that promotes formation of hydrocarbons with a target chain length as the most predominant hydrocarbon, etc.). However, in some variations, a low-alpha catalyst (e.g., associated with an alpha less than 0.5) can be used and/or beneficial (e.g., when zeolites or other catalyst substrates with particular pore sizes are used to constrain a chain length; to form olefins, alkynes, etc.; etc.). Examples of high-alpha catalysts include: cobalt catalysts (e.g., cobalt metal, cobalt nanoparticles, cobalt particles, etc.), ruthenium catalysts, nickel catalysts, and/or any suitable catalysts. Examples of low-alpha catalysts include iron catalysts, and/or any suitable catalysts. The catalysts can include one or more support, promoter (e.g., oxidation promoter, reduction promoter, etc.), and/or any suitable components. Examples of promoter materials include: silica, alkali metals (e.g., lithium, sodium, potassium, ruthenium, caesium, etc.), noble metals (e.g., copper, silver, gold, platinum, ruthenium, rhodium, osmium, iridium, palladium, etc.), and/or any suitable promoter materials. Examples of support materials include: zeolites, silica, alumina, titania, and/or any suitable support material or substrate can be used (and/or the catalyst can be used unsupported or without a support). As an illustrative example, the FT process can use a $\gamma\text{-}Al_2O_3$ support impregnated with a Co catalyst containing up to 20% Pt, Ag, or other noble metal. However, any suitable catalyst can be used.

The FT process is preferably performed at a temperature between about 200 and 350° C. (e.g., 200° C., 220° C., 230° C., 250° C., 275° C., 300° C., 310° C., 325° C., 350° C., values or ranges therebetween, etc.), but can be performed at a temperature less than 200° C. or greater than 350° C.

The FT process is preferably performed at a pressure between about 10 and 30 bar (e.g., 10 bar, 12 bar, 15 bar, 17 bar, 20 bar 22 bar, 25 bar, 27 bar, 30 bar, values or ranges therebetween, etc.), but can be performed at a pressure less than 10 bar or greater than 30 bar.

The FT process is preferably performed using syngas with a hydrogen to carbon monoxide ratio that is between about 1.8 and 2.5 (e.g., 1.8, 1.9, 2, 2.05, 2.1, 2.15, 2.2, 2.25, 2.3, 2.4, 2.5, values or ranges therebetween, etc. where the ratio can refer to a weight ratio, mass ratio, volume ratio, stoichiometric ratio, etc.), but can be performed with an $H_2$:CO ratio that is less than 1.8 or greater than 2.5. Hydrogen used in the FT process can be produced on site, can be received (e.g., as described in S130), and/or can be from any suitable source.

The gas hourly space velocity of the FT process is preferably between about 1 and 10 L/hr/(gram of catalyst), but can be less than 1 L/hr/g-catalyst or greater than 10 L/hr/g-catalyst. The weight hourly space velocity of the FT process is preferably between about 0.5 and 25, but can be less than 0.5 or greater than 25. A time on stream of the FT process can be 1-336 hours (e.g., 60-120 hrs), less than 1 hours, or greater than 336 hours.

In an illustrative example of a Ziegler process, a trialkyl-metal catalyst may be generated at elevated temperature and pressure (e.g., 120° C. and 100 bar) in the presence of hydrogen gas in a reactor (e.g., stainless steel reactor). The catalyst can be activated with ethylene, propylene, buten-3-ol, butadiene, vinyl acetylene, and/or any suitable carbon feedstock (e.g., to produce a desired hydrocarbon terminal group). The catalyst may be transferred into a gas phase reactor at elevated temperature (e.g., 50-150° C.) and elevated pressure (e.g., 1-20 bar). Ethylene and/or acetylene gases may be fed into the reactor. The relative amounts of ethylene to acetylene may range between 100% ethylene and 100% acetylene depending on the target degree of unsaturation of the resulting hydrocarbon. However, the Ziegler process can be performed in any manner.

Processing the hydrocarbons S190 can function to modify a chain length (e.g., a chain length distribution) of the hydrocarbons, remove impurities from the hydrocarbons, and/or can otherwise process the hydrocarbons. The hydrocarbons can be processed in the same reactor that the hydrocarbons are synthesized in and/or in any suitable reactor (e.g., a processing reactor, washing reactor, etc.).

Processing the hydrocarbons can include: purifying the hydrocarbons, separating the hydrocarbons, cracking the hydrocarbons, hydrogenating the hydrocarbons, and/or any suitable processing steps. These steps can be performed more than once, in any order, can be optional (e.g., depending on the hydrocarbon sample as synthesized), and/or can be performed in any manner and/or with any relationship.

Purifying the hydrocarbon can function to remove one or more impurities or other undesirable species (e.g., undesired chain lengths, undesired isomers, undesired hydrocarbons, residual reactants, residual catalyst, etc.) from the hydrocarbon sample. Purifying the hydrocarbons can include washing the hydrocarbons, distilling the hydrocarbons, fractionating the hydrocarbons, and/or any suitable process. The hydrocarbons can be washed with a solvent, surfactant, and/or any suitable species. Exemplary solvents include: water, acetone, ethanol, hexane, toluene, isopropyl alcohol, ethyl acetate, butyl acetate, methyl isobutyl ketone, dioxane, benzene, and/or any suitable solvents can be used. In variants of washing the hydrocarbons, the hydrocarbons can be sequentially (or simultaneously) washed with a plurality of solvents (e.g., in order of increasing solvent polarity, decreasing solvent polarity, etc.). The solvents used to wash the hydrocarbons can depend on the species to be removed. In some variants, acids and/or bases can be used to promote removal of trace amounts of metals (e.g., residual catalyst, from the as received feedstocks, etc.) in the hydrocarbon. As an illustrative example, the hydrocarbons can be washed using water.

Fractionating the hydrocarbons can function to modify the distribution of carbon chain lengths within the hydrocarbon sample, to isolate particular hydrocarbon chain lengths, and/or can otherwise function. The hydrocarbons can be fractionated using fractional distillation (e.g., short path distillation), using solvents (e.g., supercritical fluid fractionation, solvent fractionation such as using a solvent or solvent combination from solvents as described above, etc.), crystallization (e.g., static crystallization), winterization, and/or in any manner.

The hydrocarbon sample can be distilled, for example, by heating the hydrocarbon sample to a distillation temperature. The distillation temperature can be selected to melt hydrocarbons of a target chain length, vaporize hydrocarbons of a target chain length, and/or can otherwise be selected. In these examples, vaporized hydrocarbons can be captured (e.g., for use in downstream processes such as to be oxidized, recycled in a FT or other hydrocarbon synthesis process, for use in other processes, etc.), liquified hydrocarbons can be captured (e.g., for use in downstream processes such as to be oxidized, recycled in a FT or other hydrocarbon synthesis process, for use in other processes, etc.), solid hydrocarbons can be captured (e.g., for use in downstream processes such as to be oxidized, recycled in a FT or other hydrocarbon synthesis process, cracked to form smaller chain hydrocarbons, for use in other processes, etc.), and/or any suitable combination of distillates can be retained and/or discarded. In some variations, a distillation column can be used that achieves a temperature gradient where different hydrocarbons undergo a phase transition at different portions of the distillation column (e.g., to fractionate the hydrocarbons into different chain lengths). Separating the hydrocarbons can function to separate byproducts or other undesirable species from the hydrocarbons. For example, branched hydrocarbons (e.g., isoalkanes) can be separated from unbranched hydrocarbons, which can be preferable as branched fatty acids can be toxic (e.g., in high concentration, depending on the structure, etc.). In this example, crystallization, distillation, and/or any suitable process(es) can be used to separate the branched isomers from the unbranched isomers. In some variants, the branched isomers can be recycled in the method (e.g., can be gasified). However, the branching isomers can be oxidized and/or can otherwise be used or treated. Similarly, unsaturated hydrocarbons can be separated from saturated hydrocarbons (e.g., to hydrogenate the unsaturated hydrocarbons thereby converting them to saturated hydrocarbons).

Cracking the hydrocarbons can function to modify a chain length and/or isomerization of the hydrocarbons. During and/or after cracking the hydrocarbon sample, the cracked hydrocarbon sample is preferably predominantly (e.g., >90%, >95%, >97%, >98%, >99%, >99.5%, >99.9%, >99.95%, >99.99%, 100%, etc.) straight chain. Similarly, after cracking the hydrocarbons are preferably predominantly alkanes, but can include any suitable unsaturated hydrocarbons. However, the cracked hydrocarbons can have any suitable structure. Cracking the hydrocarbons can include: thermal cracking, steam cracking, fluid catalytic cracking, hydrocracking, and/or any suitable cracking process can be used. The hydrocarbons can be cracked using a solid acid catalyst (e.g., silica-alumina catalyst, zeolite catalyst, ZSM-5, etc.) and/or any suitable catalyst can be used. The hydrocarbons can be cracked at a temperature between about 300° C. and 1000° C., a temperature less than 300° C., and/or a temperature greater than about 1000° C. The hydrocarbons can be cracked at a pressure between about 1 bar and 100 bar, less than 1 bar, and/or greater than 100 bar. However, the hydrocarbons can be cracked in any manner. In some variants, a subset of the hydrocarbons can be cracked. For instance, when a target chain length distribution is C16-C40, hydrocarbons of the sample with greater than 40 carbon atoms (e.g., C41 and/or greater) can be cracked, where the long chain hydrocarbons can be separated as described above. In another example, odd hydrocarbons with odd chain lengths can be cracked (e.g., where even chain hydrocarbons can be recovered for the hydrocarbon sample). However, the entire hydrocarbon sample can be cracked (e.g., to modify the chain length distribution, to achieve a target chain length distribution, etc.) and/or any suitable hydrocarbons (or subset thereof) can be cracked.

Hydrogenating the hydrocarbons functions to hydrogenate or saturate unsaturated hydrocarbons of the synthesized hydrocarbons. The hydrocarbons are preferably fully hydrogenated (e.g., form saturated hydrocarbons), but can be partially hydrogenated (preferably but not necessarily with the remaining unsaturated sites having a cis configuration). The hydrocarbons can be hydrogenated, for instance, in the presence of a platinum, palladium, rhodium, ruthenium, nickel (e.g., Raney nickel, Urushibara nickel, etc.), and/or using any suitable catalyst. The catalyst can be heterogeneous or homogeneous. However, the hydrocarbons can be hydrogenated in any manner.

Oxidizing the hydrocarbon sample S200 functions to form oxygenated hydrocarbons. The oxygenated hydrocarbons are preferably monocarboxylic acids but can additionally or alternatively include other oxygenated (by) products such as: alcohols, ketones, aldehydes, polycarboxylic acids (e.g., diacids), lactones, and/or any suitable species. The hydrocarbon sample can be oxidized in the same or a different reactor from a reactor used for the formation of the hydrocarbon sample. The hydrocarbon sample to be oxidized can include hydrocarbons, oxygenated hydrocarbons (e.g., from the Ziegler process, from prior instances of oxidizing hydrocarbons, etc.), processed hydrocarbons, synthesized hydrocarbons, received hydrocarbons, and/or any suitable species. In some variants, the hydrocarbon sample can include upto 100% (e.g., 10%, 20%, 30%, 40%, 50%, 60%, 70%, 80%, 90%, values or ranges therebetween, etc.) recycled hydrocarbons (e.g., hydrocarbons or partially-oxygenated hydrocarbons from previous oxidation processes). For example, a straight-chain paraffin sample can be oxidized. However, any suitable hydrocarbon sample can be oxidized.

Figure 5A:
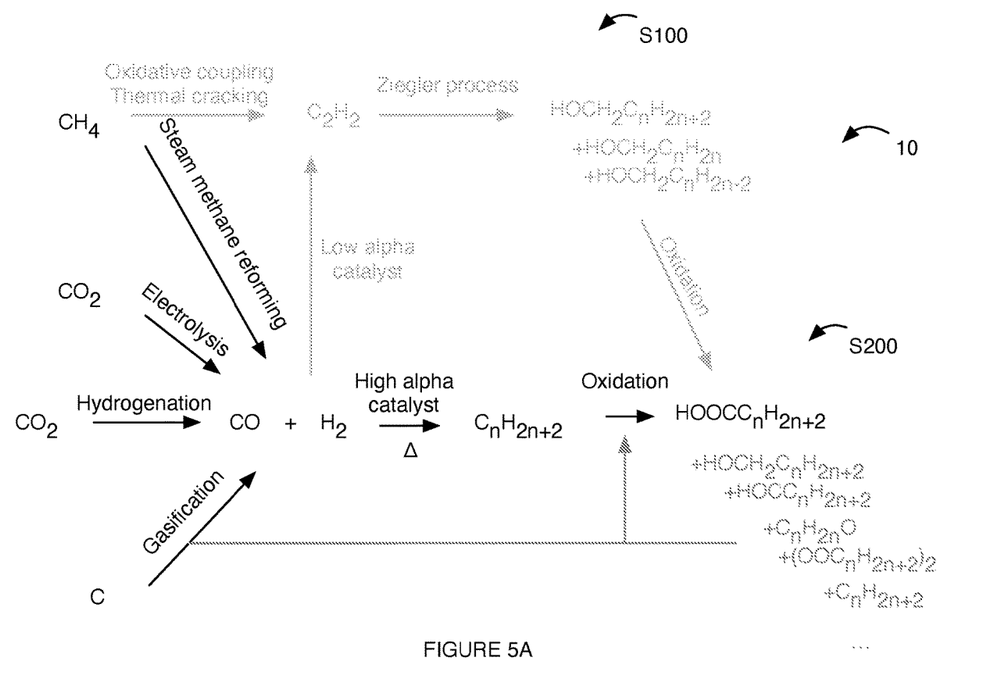
FIGS. 5A and 5B are a schematic representation of an exemplary variant of the method.
Figure 5B:
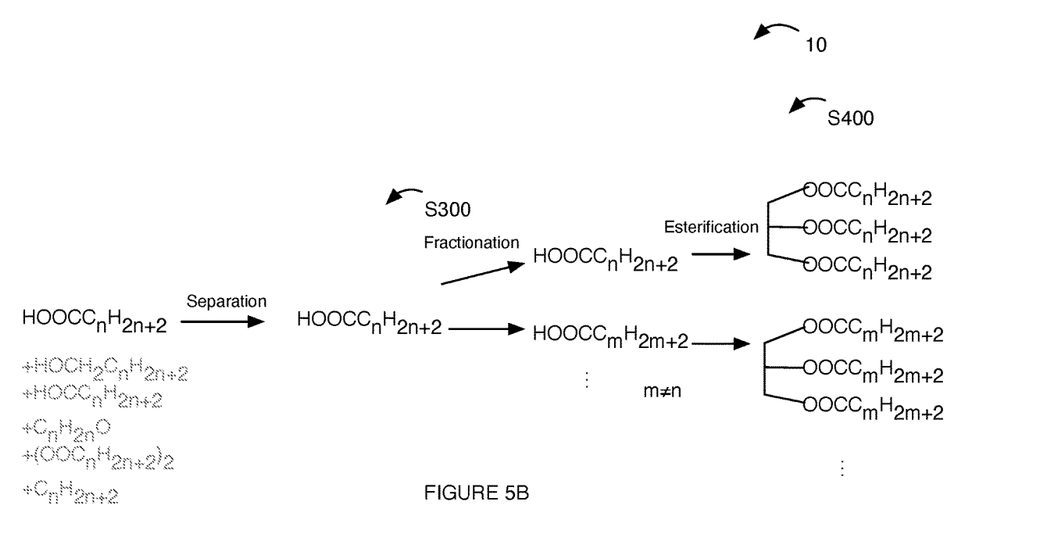

The oxidation conditions used for oxidizing the hydrocarbons preferably avoid overoxidizing the hydrocarbons. For instance, the conditions are preferably selected to form alcohols (e.g., primary alcohols, monohydric alcohols, etc.), aldehydes (e.g., monoaldehydes), monocarboxylic acids, and/or other oxygenated species where a single carbon atom in the chain (e.g., preferably but not necessarily a primary or terminal carbon atom) is bonded to an oxygen atom. Similarly, the conditions are preferably selected to avoid formation of polyhydric alcohols, ketones, polycarboxylic acids, lactones, and/or other oxygenated species where a plurality of carbon atoms are bonded to oxygen and/or a secondary (or higher order) carbon atom is bonded to an oxygen atom. As a result, the oxidation reaction is frequently incomplete and some (e.g., 5%, 10%, 20%, 30%, 40%, 50%, 60%, 70%, 80%, values or ranges therebetween etc.) of the initial hydrocarbons can remain unreacted. These unreacted hydrocarbons can then be recycled (e.g., have S200 performed on them again, be mixed with a second hydrocarbon sample that is to be oxidized, gasified, etc.), discarded, and/or can otherwise be used. Similarly, underoxidized species (e.g., aldehydes, primary alcohols, etc.) can be recycled in the oxidation reaction, for gasification, and/or can otherwise be recycled and/or used. Overoxidized species (e.g., ketones, polyhydric alcohols, secondary alcohols, tertiary alcohols, lactones, etc.) can be reduced (e.g., via hydrogenation) where the reduced species can be oxidized again, can be gasified (e.g., to form carbon feedstock, as shown for example in FIG. 5B, etc.), and/or can otherwise be used.

The hydrocarbon sample is preferably oxidized at a temperature between about 90-400° (e.g., 90-150° C.), but can be performed at a temperature less than 90° C. or greater than 400° C. The hydrocarbon sample is preferably oxidized at a pressure between about 1 and 25 bar, but can be oxidized at a pressure less than 1 bar and/or greater than 25 bar. The hydrocarbon sample can be oxidizing using air, oxygen (e.g., pure oxygen such as oxygen with a purity of 90%, 95%, 97%, 98%, 99%, 99.5%, 99.9%, 99.95%, 99.99%, 99.995%, 99.999%, 99.9999%, 100%, etc.), and/or any suitable oxygen source can be used. The flow rate (e.g., of the oxygen component of the oxidant) is preferably between 10 sccm/20 gram hydrocarbon and 1000 sccm/20 gram hydrocarbon (e.g., 10 sccm/20 gram hydrocarbon, 20 sccm/20 gram hydrocarbon, 40 sccm/20 gram hydrocarbon, 50 sccm/20 gram hydrocarbon, 100 sccm/20 gram hydrocarbon, 200 sccm/20 gram hydrocarbon, 400 sccm/20 gram hydrocarbon, 500 sccm/20 gram hydrocarbon, 1000 sccm/20 gram hydrocarbon, values or ranges therebetween, etc.) but can be less than 10 sccm/20 gram hydrocarbon or greater than 1000 sccm/20 gram hydrocarbon. For example, when air is used to oxidize the hydrocarbon sample, a flow rate can be about 200 sccm/20 gram hydrocarbon. The hydrocarbon sample is preferably rigorously stirred during oxidation (e.g., using mechanical impellers, vigorous bubbling, etc.).

The hydrocarbon sample can be oxidized in the presence of a catalyst and/or oxidized without using a catalyst. The catalyst can be heterogeneous or homogeneous. Exemplary catalysts include: permanganate (e.g., potassium permanganate), iron catalyst, copper catalyst, phenacylamine catalyst, soluble catalyst (e.g., manganese soaps), and/or using any suitable catalyst (e.g., other transition metal catalysts with or without support materials). In some variants, the catalyst can be dispersed in the hydrocarbon (e.g., through rigorous stirring such as by bubbling gas through the hydrocarbon, using mechanical impellers, etc.). The catalyst can be dispersed in the hydrocarbon prior to and/or at the same time as the hydrocarbon is oxidized.

The hydrocarbon sample can be maintained in the oxidation conditions for between 1 minutes and 240 hours. However, the hydrocarbon sample can be maintained in the oxidation conditions for any suitable amount of time. Some variants of the method can select oxidation parameters to obtain a shorter oxidation time, which can be beneficial for avoiding overoxidation (e.g., multi-oxidation events), decreasing operation expenses and/or power usage (e.g., from maintaining a target temperature and/or pressure for the reaction). As an example, the oxidizing agent (e.g., air, oxygen, etc.) can be mixed with the hydrocarbon (e.g., injected) as bubbles (e.g., with a diameter between about 0.5-500 μm).

In some variants, process parameters (e.g., temperature, airflow, pressure) can be controlled and/or changed in response to compositional changes of the chemical mixture in the oxidation vessel. For example, the reaction can be terminated once the mixture contains a predetermined fraction of a product, as running the reaction longer can lead to lower yields, or the production of undesired molecules. As another example, it may be desirable to ramp the temperature of the mixture immediately upon detection of water, which can be an indication of reaction initiation. To enable such adaptive control over the process parameters, a feedback system can be implemented which leverages one or more "in-situ diagnostic probes".

Examples of in-situ diagnostic probes include: optical probes (e.g., spectroscopic probes, colorimetric probes, transmission probes, reflection probes, light scattering probes, etc.), electrical probes (e.g., resistance, conductivity, etc.), molecular composition (e.g., carbon sensors, carbon monoxide sensors, carbon dioxide sensors, etc.), temperature probes, pressure probes, and/or any suitable probes or sensors can be used.

In a first illustrative example, the intensity of light transmitted through or reflected by the chemical mixture in the oxidation vessel. For instance, a spectroscopic measurement at ultraviolet, visible, near-infrared, or mid-infrared wavelengths could yield compositional information about the fatty acid content of the mixture (e.g., a mixture containing fatty acids or certain impurities may appear more yellow or amber than the starting mixture of alkanes, which may appear colorless in the visible spectrum). Such an optical measurement may be performed through an optical window in the reaction vessel.

In a second illustrative example, the electrical resistivity of the chemical mixture can be measured. For example, at DC or relatively low frequency (e.g. kHz), the electrical conductivity of a mixture of alkanes may be nearly zero, whereas certain fatty acids may have nonzero DC or low-frequency electrical conductivity. In this way, monitoring the electrical conductivity of the chemical mixture may yield useful information about the presence of certain chemical species. The electrical conductivity may be monitored, for instance, using metallic electrodes and monitoring the current flowing between them in response to an applied voltage. The applied voltage and resulting current should be small enough to not perturb the chemical reaction. To achieve a lower noise on the measurement of the conductivity, a lock-in amplifier may preferably be used to apply a low-frequency AC voltage between the electrodes and measure the low-frequency AC current.

In a third illustrative example, the $CO_2$ concentration of the output stream from the reaction vessel can be measured. The $CO_2$ concentration (as well as other gases such as CO, $H_2O$, etc.) may be monitored with a continuous emissions monitoring system which dries and separates the gases from the volatile organics and analyzes their concentration in an inline unit such as a gas chromatograph.

As one specific example of the usage of in-situ diagnostics to improve reaction yield, the $CO_2$ concentration of the output stream from the reaction vessel can be monitored along with the color of the liquid reaction mixture; the temperature and gas flow parameters can be adjusted to optimize yield of fatty acids (e.g. temperature is lowered and/or gas flow is increased if color of chemical mixture is too dark, gas flow is lowered if $CO_2$ concentration is too high).

In some variants, waste heat from the hydrocarbon synthesis can be used to heat the hydrocarbon sample during oxidation.

Processing the oxidized hydrocarbons S300 functions to separate, fractionate, purify, and/or otherwise functions to process the oxidized hydrocarbons. The oxidized hydrocarbons can be processed in the same and/or a different location as the hydrocarbons are oxidized. The oxidized hydrocarbons can be processed in the same or a different reactor as the hydrocarbons are oxidized in and/or the hydrocarbons are synthesized or processed in. The oxidized hydrocarbons can be processed immediately after the hydrocarbons are oxidized, a threshold time after the hydrocarbons have been oxidized (e.g., after the oxidized hydrocarbons have cooled to room temperature, have reached a threshold temperature, etc.; 1 min, 5 min, 10 min, 20 min, 30 min, 60 min, 90 min, 120 min, 200 min, 300 min, 8 hr, 12 hr, 24 hr, 36 hr, 48 hr, 72 hr, 96 hr, 120 hr, 240 hr, 300 hr, etc.; etc.), and/or with any suitable timing.

The oxidized hydrocarbons can be processed in the same and/or a different manner as the hydrocarbons (e.g., as described in S190). For instance, processing the oxidized hydrocarbons can include purifying the oxidized hydrocarbons, separating the oxidized hydrocarbons, fractionating the oxidized hydrocarbons, cracking the oxidized hydrocarbons, and/or any suitable processing steps.

Purifying the oxidized hydrocarbons can function to remove one or more impurities or other undesirable species (e.g., undesired chain lengths, undesired isomers, undesired hydrocarbons, residual reactants, residual catalyst, etc.) from the oxidized hydrocarbon sample. Purifying the oxidized hydrocarbons can include washing the oxidized hydrocarbons, distilling the oxidized hydrocarbons, fractionating the oxidized hydrocarbons, and/or any suitable process. The oxidized hydrocarbons can be washed with a solvent, surfactant, and/or any suitable species. Exemplary solvents include: water, acetone, ethanol, hexane, toluene, isopropyl alcohol, ethyl acetate, butyl acetate, methyl isobutyl ketone, dioxane, benzene, and/or any suitable solvents can be used. In variants of washing the oxidized hydrocarbons, the oxidized hydrocarbons can be sequentially (or simultaneously) washed with a plurality of solvents (e.g., in order of increasing solvent polarity, decreasing solvent polarity, etc.). The solvents used to wash the oxidized hydrocarbons can depend on the species to be removed. In some variants, acids and/or bases can be used to promote removal of trace amounts of metals (e.g., residual catalyst, from the as received feedstocks, etc.) in the oxidized hydrocarbon. As an illustrative example, the oxidized hydrocarbons can be washed using water.

Fractionating the oxidized hydrocarbons can function to modify the distribution of carbon chain lengths within the oxidized hydrocarbon sample, to isolate particular oxidized hydrocarbon chain lengths, and/or can otherwise function. The oxidized hydrocarbons can be fractionated using fractional distillation (e.g., short path distillation), using solvents (e.g., supercritical fluid fractionation, solvent fractionation such as using a solvent or solvent combination from solvents as described above, etc.), crystallization (e.g., static crystallization), using an evaporation process (e.g., falling-film evaporation, wiped film evaporation, etc.), winterization, and/or in any manner. For example, after fractionation, oxidized hydrocarbons with each chain length can be isolated (e.g., into individual fatty acid components). As an illustrative example, when an oxidized hydrocarbon sample includes hydrocarbons with C18 to C28, the sample can be fractionated into separate C18, C19, C20, C21, C22, C23, C24, C25, C26, C27, and C28 samples (where each sample is predominantly composed of a single carbon chain length). However, the oxidized hydrocarbon samples can otherwise be fractionated.

The oxidized hydrocarbon sample can be distilled, for example, by heating the oxidized hydrocarbon sample to a distillation temperature and/or pressurizing the sample (e.g., using pressurized distillation). The distillation temperature can be selected to melt oxidized hydrocarbons of a target chain length, vaporize oxidized hydrocarbons of a target chain length, to melt specific oxidized hydrocarbon species (e.g., carboxylic acids, alcohols, ketones, aldehydes, etc.), vaporize specific oxidized hydrocarbon species (e.g., carboxylic acids, alcohols, ketones, aldehydes, etc.), and/or can otherwise be selected. In these examples, vaporized oxidized hydrocarbons can be captured (e.g., for use as a fatty acid, to be recycled in an additional oxidation step, for use in other processes, to be recycled as a carbon feedstock, etc.), liquified oxidized hydrocarbons can be captured (e.g., for use as a fatty acid, to be recycled in an additional oxidation step, for use in other processes, to be recycled as a carbon feedstock, etc.), solid oxidized hydrocarbons can be captured (e.g., for use as a fatty acid, to be recycled in an additional oxidation step, for use in other processes, to be recycled as a carbon feedstock, etc.), and/or any suitable combination of distillates can be retained and/or discarded. In some variations, a distillation column can be used that achieves a temperature gradient where different oxidized hydrocarbons undergo a phase transition at different portions of the distillation column (e.g., to fractionate the oxidized hydrocarbons into different chain lengths, different oxidized species, etc.).

Figure 3:
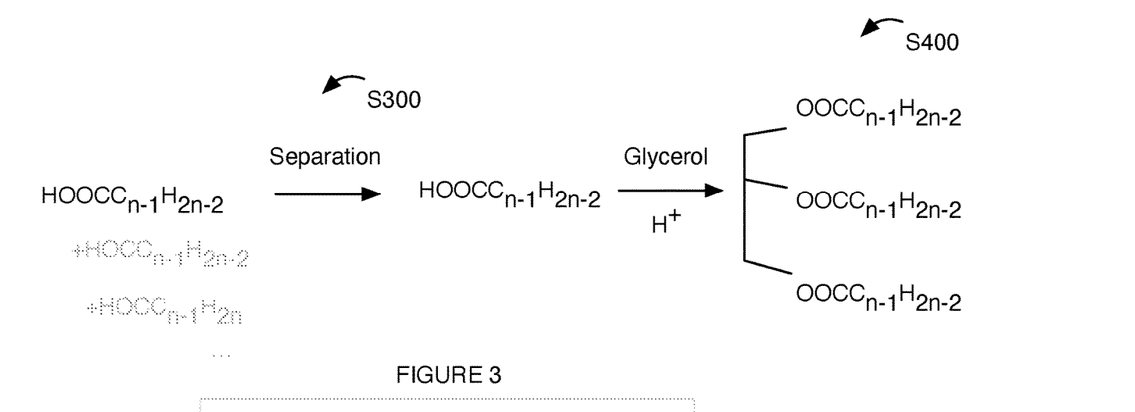
FIG. 3 is a schematic representation of an example of processing an oxygenated paraffin and esterifying the oxygenated paraffins.

Separating the oxidized hydrocarbons can function to separate byproducts or other undesirable species (e.g., partially oxidized hydrocarbons, overoxidized hydrocarbons, etc.) from the oxidized hydrocarbons. For example (e.g., as shown for instance in FIG. 3), carboxylic acids can be separated from unoxidized hydrocarbons and/or other oxygenated hydrocarbons, which can be beneficial for recycling species (e.g., to improve an overall yield), to isolate fatty acids, and/or can otherwise be beneficial. In this example, saponification, esterification, crystallization, distillation, and/or any suitable process(es) can be used to separate the carboxylic acids from other hydrocarbons or oxygenate species.

In variants using saponification, saponification can be performed, for instance, by mixing the oxidized hydrocarbons with a base (e.g., lithium hydroxide, sodium hydroxide, potassium hydroxide, rubidium hydroxide, caesium hydroxide, beryllium hydroxide, magnesium hydroxide, calcium hydroxide, strontium hydroxide, barium hydroxide, aluminium hydroxide, ammonia, sodium bicarbonate, potassium bicarbonate, ammonium bicarbonate, etc. such as with a concentration between about 0.01 M and 20 M) such as 0.05-2× base solution by volume relative to the volume of oxygenated hydrocarbon. In these variants, the carboxylic acids can be deprotonated and phase separated into an aqueous phase while other oxygenated species can be more soluble in a nonpolar or organic phase. The saponification can be performed at an elevated temperature (e.g., between about 30-200° C. such as 50° C., 75° C., 100° C., 120° C., 150° C., 180° C., etc.), at or near room temperature (e.g., 0° C.-30° C.), and/or at any suitable temperature (e.g., >120° C., <0° C.). The saponified sample can be rinsed with a solvent (e.g., water, ethanol, etc.). In some variations, the saponification can be performed in situ with the oxidation of the hydrocarbons (e.g., a base can be added into the oxidation reactor and/or during the oxidation reaction which can function to saponify carboxylic acids as they form). However, the saponification (and/or other separations) can be performed after the oxidation and/or with any suitable timing. After separating the carboxylic acid from other species, the carboxylic acid can be recovered, for instance, by mixing the carboxylates (e.g., soap) with an acid (e.g., with a molar equivalent of acid or protons to carboxylate ions). Exemplary acids include sulfuric acid, nitric acid, hydrochloric acid, hydrobromic acid, hydroiodic acid, and/or any suitable acid (e.g., with any suitable concentration and/or volume).

However, the carboxylic acids can otherwise be separated.

Esterifying the oxygenated hydrocarbons preferably functions to form glycerides, but can additionally or alternatively form any suitable esters of the oxygenated hydrocarbons. Fatty acids (e.g., carboxylic acids) are preferably esterified. However, additionally or alternatively, alcohols and/or any suitable oxygenated hydrocarbons can be esterified. The glycerides are preferably triglycerides, but can additionally or alternatively be (or include) di-glycerides (e.g., 1,2-diglycerides, 1,3-diglycerides) and/or monoglycerides (e.g., 1-monoglycerides, 2-monoglycerides). The polyglycerides (e.g., diglycerides, triglycerides) can be homoglycerides (e.g., include a plurality of the same fatty acid moiety, homotriglycerides, homodiglycerides, etc.) or heteroglycerides (e.g., include two or three difference fatty acid moieties, heterotriglycerides, etc.). The heteroglycerides are preferably narrow band heteroglycerides (e.g., include fatty acids with chain lengths differing by at most about 10 carbon atoms), but can be wide band heteroglycerides (e.g., include fatty acids with chain lengths differing by greater than 10 carbon atoms) and/or can include any suitable heteroglycerides (e.g., with any suitable combination of chain lengths). Thus, fractionated fatty acids (e.g., fractionated into separate chain lengths) are preferably separately esterified. However, coarse fractionated fatty acids (e.g., with a narrow distribution of chain lengths such as with a mixture of 2, 3, 5, 10, etc. fatty acids) can be esterified, unfractionated fatty acids can be esterified, and/or any suitable oxygenated hydrocarbon(s) can be esterified.

The fatty acids are preferably esterified with glycerol, but can be esterified with any suitable alcohol and/or polyol (e.g., sugar alcohols). The glycerol can be derived from natural sources, synthetically manufactured (e.g., from propene such as propene from a carbon feedstock), and/or can otherwise be derived from any suitable starting material(s) or resources.

The fatty acids can be esterified using Fischer esterification (e.g., treating the carboxylate with an alcohol in the presence of a dehydrating agent preferably in acidic conditions), Steglich esterification, Mitsunobu reaction, using epoxides, using alcholysis (e.g., converting the fatty acid to an acyl halide or acid anhydride which is reacted with an alcohol), alkylation of carboxylate anions (e.g., reacting carboxylates of the fatty acid such as generated using a base with an alkyl halide), using the Tishchenko reaction (e.g., to convert recovered aldehydes into esters), interesterifcation (e.g., between glycerides of different fatty acids), and/or using any suitable methods.

As an illustrative example, a fatty acid (e.g., coarse fraction, single fatty acid, etc.) can be esterified using a stoichiometric amount of glycerol and/or an excess of glycerol or fatty acid). For instance, 3-5 equivalents of fatty acid per glycerol can be used in the esterification process. The esterification can be performed in the presence of a catalyst (e.g., sulfuric acid, magnesium oxide, tin, zinc, alumina, etc. such as at 0.5-5 wt %). The esterification can be performed at or near room temperature, at an elevated temperature (e.g., between 30° C. and 300° C.), and/or at any suitable temperature. The esterification can be performed at or near standard pressure (e.g., approximately 1 bar), at reduced pressures (e.g., 0.01 bar to 1 bar), and/or at elevated pressure (e.g., greater than 1 bar). The esterification is preferably performed in an inert atmosphere (e.g., an inert gas such as nitrogen, helium neon, argon, krypton, xenon, carbon dioxide, etc.; vacuum such as at a pressure less than or about 1 hPa, 5 hPa, 10 hPa, 50 hPa, 0.1 kPa, 0.5 kPa, 1 kPa, values or ranges therebetween, etc.; etc.), but can be performed in an oxidizing, reducing, or otherwise reactive atmosphere (e.g., to regenerate a catalyst, to react with or remove byproducts, etc.). Performing the reaction in an inert environment can be beneficial for limiting (e.g., minimizing, decreasing, reducing, etc.) discoloration in the resulting triglyceride. For instance, nitrogen (or other inert gases) can be vigorously bubbled or flowed during the esterification process. The esterification can be performed in a multistep process (e.g., with different catalysts in each step such as tin or zinc for a first step and alumina for a second step, with different temperature in each step such as a higher subsequent temperature, with different pressure in each step, etc.) and/or in a single step.

Esterification of the oxygenated hydrocarbons can include processing the oxygenated hydrocarbons. For instance, the oxygenated hydrocarbons can be purified, interesterified, and/or processed in any manner. Examples of purification processes that can be performed on the esters include: extractions (e.g., with strong acids such as 20% sulfuric acid, with strong base such as 35% sodium hydroxide) which can be beneficial for removing some catalysts (e.g. zinc, tin) or free fatty acids, washing the ester(s) with high temperature steam (e.g., 260-360° C.) which can be beneficial for removing free fatty acid(s) and/or free glycerol, treatment with activated carbon, treatment with bleaching earth, distillation, and/or any suitable purification process (es) (e.g., purification processes as described for hydrocarbons, oxygenated hydrocarbons, etc.). In some variants, the esters can be purified at elevated temperature (e.g., 240-260° C.) to facilitate and/or improve an efficiency of purification (e.g., reduce a number of purification steps necessary, increase a yield after purification, etc.). Similarly, in some variants, the esters (e.g., glycerides) can be fractionated.

As an illustrative example of the method (as shown for instance in FIG. 5A and FIG. 5B), the method for forming fatty acids can include: receiving a carbon feedstock (e.g., one or more of methane, carbon dioxide, carbon, coal, carbon monoxide, etc.), converting the carbon feedstock to carbon monoxide to form syngas (e.g., via electrolysis, steam methane reforming, gasification, hydrogenation, reduction, etc.), using a high-alpha catalyst Fischer-Tropsch reaction to produce a paraffin sample, separating byproducts (e.g., branching paraffins, olefins, etc.) from the paraffin sample, oxidizing the paraffin sample (e.g., excluding the byproducts, including the byproducts, etc.), separating carboxylic acids from other byproducts of the oxidation (e.g., unreacted paraffins, alcohols, ketones, aldehydes, lactones, diacids, etc.), optionally fractionating the fatty acids (e.g., into separate chain lengths, into coarse fractions, etc.), and esterifying the fatty acids (e.g., with glycerol). In this illustrative example, the byproducts (e.g., of the Fischer-Tropsch process, of the oxidation, etc.) can be recycled (e.g., via gasification, to be further oxidized, etc.). In variations of this specific example, methane and/or syn gas can be used to generate alkenes and/or alkynes (e.g., via oxidative coupling, thermal cracking, Fischer-Tropsch process using a low-alpha catalyst such as an iron catalyst, etc.) which can be used in a Ziegler process to form fatty alcohols, the fatty alcohols can then be oxidized (e.g., with the paraffins from the Fischer-Tropsch process, or separate from the paraffins) to form fatty acids (which, if separate, can be combined with the oxygenated hydrocarbons formed from the paraffins). However, the method can include any suitable steps in any suitable order. In this illustrative example, one or more of: propionic acid, butyric acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, carboceric acid, montanic acid, nonacosylic acid, melissic acid, hentriacontylic acid, lacceroic acid, psyllic acid, geddic acid, ceroplastic acid, hexatriacontylic acid, heptatriacontylic acid, octatriacontylic acid, nonatriacontylic acid, tetracontylic acid, and/or any suitable fatty acid (or glyceride derived from combinations thereof). The relative amounts of different acids can depend on the paraffin starting material, a catalyst (e.g., used in the paraffin synthesis), a fractionation process, a separation process, a reaction parameter (e.g., temperature, space velocity, pressure, etc.), and/or can otherwise be controlled.

The methods of the preferred embodiment and variations thereof can be embodied and/or implemented at least in part as a machine configured to receive a computer-readable medium storing computer-readable instructions (e.g., to automate the performance of chemical tasks). The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

Embodiments of the system and/or method can include every combination and permutation of the various system components and the various method processes, wherein one or more instances of the method and/or processes described herein can be performed asynchronously (e.g., sequentially), concurrently (e.g., in parallel), or in any other suitable order by and/or using one or more instances of the systems, elements, and/or entities described herein.

As a person skilled in the art will recognize from the previous detailed description and from the figures and claims, modifications and changes can be made to the preferred embodiments of the invention without departing from the scope of this invention defined in the following claims.

We claim:

1. A method for producing a triglycerides comprising:
reducing carbon dioxide to carbon monoxide using hydrogenation;
preparing paraffins with a distribution of carbon atoms between about 6 and 100 via a Fischer-Tropsch reaction between the carbon monoxide and hydrogen in a presence of a high-alpha catalyst;
cracking the paraffins to generate cracked paraffins, wherein a cracked paraffin of the cracked paraffins comprises between 18 and 28 carbon atoms;
separating unbranched paraffins from branched paraffins of the cracked paraffins using crystallization;
oxidizing, at a temperature between about 90 and 150° C., the unbranched paraffins to form fatty acids;
separating the fatty acids from other oxidation byproducts to generate separated fatty acids;
esterifying the separated fatty acids with glycerol to form the triglycerides.

2. The method of claim 1, wherein the high-alpha catalyst comprises a cobalt catalyst.

3. The method of claim 1, wherein an alpha parameter of a distribution of the paraffins is greater than about 0.8.

4. The method of claim 1, wherein hydrogen used for either reducing the carbon dioxide or for the Fisch-Tropsch reaction comprises at least one of: green hydrogen, turquoise hydrogen, purple hydrogen, pink hydrogen, red hydrogen, yellow hydrogen, or white hydrogen.

5. The method of claim 1, wherein at least 70% of carbon atoms from the carbon dioxide are converted into the fatty acids.

6. The method of claim 1, further comprising oxidizing the other oxidation byproducts and unreacted unbranched paraffins remaining after the oxidizing the unbranched paraffins.

7. A method for producing a triglyceride comprising:
receiving a paraffin sample, wherein the paraffin sample is manufactured by at least one of:
generating a carbon monoxide feedstock by comprising reducing carbon dioxide using either hydrogenation;
performing a Fischer-Tropsch process on the carbon monoxide feedstock using a high-alpha catalyst to form paraffins with between 6 and 100 carbon atoms; and
at least one of cracking or distilling the paraffins to form the paraffin sample, wherein paraffins of the paraffin sample comprise a target range of carbon atoms;
oxidizing the paraffin sample to form fatty acids;
fractioning the fatty acids to form fractionated fatty acids; and
esterifying the fractionated fatty acids with glycerol to form triglycerides.

8. The method of claim 7, wherein the triglycerides comprise fatty acids with chain lengths differing by at most 10 carbon atoms.

9. The method of claim 7, wherein hydrogen used for either reducing the carbon dioxide or for the Fisch-Tropsch process comprises at least one of: green hydrogen, turquoise hydrogen, purple hydrogen, pink hydrogen, red hydrogen, yellow hydrogen, or white hydrogen.

10. The method of claim 7, wherein cracking the paraffins comprises hydrocracking the paraffins at a temperature between 200° C. and 350° C. in a presence of a platinum supported ZSM-5 catalyst.

11. The method of claim 10, wherein receiving the paraffin sample further comprises fractionating the paraffin sample, wherein paraffins of the paraffin wax sample with a carbon number less than 16 or greater than 40 are removed from the paraffin sample.

12. The method of claim 11, wherein the paraffins with the carbon number greater than 40 are recycled and cracked.

13. The method of claim 7, wherein the high-alpha catalyst comprises a cobalt catalyst.

14. The method of claim 7, further comprising separating the fatty acids from unreacted paraffins and partially oxidized paraffins.

15. The method of claim 14, wherein the unreacted paraffins and the partially oxidized paraffins are recycled and oxidized with a second paraffin sample.

16. The method of claim 15, wherein the second paraffin sample is substantially identical to the paraffin sample.

17. The method of claim 7, wherein manufacturing the paraffin sample further comprises removing branched paraffins from the paraffin sample using crystallization.

18. The method of claim 17, wherein manufacturing the paraffin sample further comprises fully hydrogenating olefins in the paraffin sample.

19. The method of claim 7, wherein at least 40% of carbon atoms from the carbon monoxide feedstock are converted into the triglycerides.

20. The method of claim 7, wherein the target range of carbon atoms is between 16 and 40 carbon atoms.

* * * * *

UNITED STATES PATENT AND TRADEMARK OFFICE
CERTIFICATE OF CORRECTION

PATENT NO. : 12,415,772 B1  
APPLICATION NO. : 17/825490  
DATED : September 16, 2025  
INVENTOR(S) : Kathleen Alexander and Ian McKay Page 1 of 1

It is certified that error appears in the above-identified patent and that said Letters Patent is hereby corrected as shown below:

In the Claims

Column 17, Claim 1, Line 18, after "producing", delete "a"

Column 17, Claim 4, Line 41, delete "Fisch-Tropsch" and insert --Fischer-Tropsch-- therefor Column 17, Claim 7, Line 55, after "by", delete "comprising"

Column 18, Claim 7, Line 1, after "using", delete "either"

Column 18, Claim 9, Line 19, delete "Fisch-Tropsch" and insert --Fischer-Tropsch-- therefor Column 18, Claim 11, Line 29, after "paraffin", delete "wax"

Signed and Sealed this  
Eleventh Day of November, 2025

John A. Squires  
*Director of the United States Patent and Trademark Office*